(12) United States Patent
Hausen et al.

(10) Patent No.: US 7,530,987 B1
(45) Date of Patent: May 12, 2009

(54) SURGICAL TOOL FOR CREATING AN INCISION IN A TUBULAR VESSEL

(75) Inventors: Bernard A. Hausen, Menlo Park, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 1479 days.

(21) Appl. No.: 10/134,081

(22) Filed: Apr. 24, 2002

(51) Int. Cl.
 *A61B 17/32* (2006.01)
(52) U.S. Cl. .................................. 606/170; 606/185
(58) Field of Classification Search ............ 606/181, 606/182, 185, 186, 187, 188, 189, 190, 167
See application file for complete search history.

(56) References Cited

U.S. PATENT DOCUMENTS

| | | | |
|---|---|---|---|
| 1,087,845 A * | 2/1914 | Stevens | 604/159 |
| 3,545,443 A * | 12/1970 | Ansari | 604/160 |
| 3,605,721 A * | 9/1971 | Hallac | 600/567 |
| 4,471,778 A * | 9/1984 | Toye | 128/207.29 |
| 4,543,966 A * | 10/1985 | Islam et al. | 600/567 |
| 4,651,752 A * | 3/1987 | Fuerst | 600/567 |
| 4,926,877 A * | 5/1990 | Bookwalter | 600/567 |
| 5,292,310 A * | 3/1994 | Yoon | 604/158 |
| 5,380,290 A * | 1/1995 | Makower et al. | 604/164.01 |
| 5,545,175 A * | 8/1996 | Abidin et al. | 606/182 |
| 5,562,241 A | 10/1996 | Knodel et al. | |
| 5,591,186 A * | 1/1997 | Wurster et al. | 606/170 |
| 5,685,856 A * | 11/1997 | Lehrer | 604/164.1 |
| 5,709,671 A * | 1/1998 | Stephens et al. | 604/264 |
| 6,113,616 A | 9/2000 | Taylor et al. | |
| 6,187,019 B1 | 2/2001 | Stefanchik | |
| 6,267,750 B1 * | 7/2001 | Utterberg | 604/264 |
| 6,346,115 B1 * | 2/2002 | Lawrence | 606/185 |
| 6,488,693 B2 * | 12/2002 | Gannoe et al. | 606/167 |
| 6,514,263 B1 | 2/2003 | Stefanchik | |
| 6,520,973 B1 | 2/2003 | McGarry | |
| 6,530,932 B1 | 3/2003 | Swayze | |
| 6,564,087 B1 * | 5/2003 | Pitris et al. | 600/478 |
| 6,716,228 B2 * | 4/2004 | Tal | 606/167 |
| 6,786,875 B2 * | 9/2004 | Barker et al. | 600/585 |

\* cited by examiner

*Primary Examiner*—Anhtuan T. Nguyen
*Assistant Examiner*—Elizabeth Houston
(74) *Attorney, Agent, or Firm*—Brian A. Schar

(57) ABSTRACT

A single tool penetrates a target vessel and cuts an incision of a known length in the vessel. The tool is easily held by the user in one hand and actuated with that single hand. The tool has features to allow for easy penetration of the target vessel as well as safety features integrated within the tool itself. User input features are located conveniently on the exterior of the tool.

9 Claims, 6 Drawing Sheets

SURGICAL TOOL FOR CREATING AN INCISION IN A TUBULAR VESSEL

FIELD OF THE INVENTION

The present invention relates generally to surgery, and more specifically to creating an accurate-length incision in the wall of a tubular structure such as a coronary blood vessel.

BACKGROUND

Anastomosis is a procedure where two separate tubular or hollow organs are surgically grafted together to form a flexible conduit. In a coronary artery bypass graft (CABG) procedure, one end of the graft vessel is usually attached to the aorta and the other to the coronary artery to bypass the blocked area and reroute blood flow to the heart. Prior to an anastomotic procedure between the coronary artery and the graft vessel, a surgeon usually creates an incision in the coronary artery before the graft vessel is attached. This incision is known as an arteriotomy. Currently, creating an arteriotomy requires the use of separate tools to penetrate the vessel and create the incision. The use of multiple tools to complete a simple task such as creating an arteriotomy can lengthen the amount of time a patient spends in the operating room. Accordingly, a need exists for a tool that is capable of performing both functions of puncturing the vessel and creating the incision within the same vessel.

SUMMARY

An integrated tool for preparing a target vessel such as the coronary artery prior to an anastomotic procedure includes features for puncturing the target vessel and creating an incision therein.

In one aspect of the invention, a needle with a sharpened endpoint is combined with a cutting member into a single tool having a housing structure. The cutting member is slidable relative to the needle. The needle and the cutting member are both held by the housing structure such that the needle is fixed at the distal end of the tool but the cutting member can travel linearly to create the incision.

In another aspect of the invention, the tip of the needle serves to penetrate the target vessel at the intended anastomosis site. The puncture serves as a first end of the incision to be created.

In another aspect of the invention, a slot in the needle guides the cutting member as it cuts through the vessel wall. The cutting member includes a nose to guide the cutting member through the vessel beginning at the point where the needle has penetrated the vessel. The translational motion of the cutting member creates an incision in the wall of the vessel as it moves through the slot in the needle.

In another aspect of the invention, the needle has a lumen that houses a tip protector. After the needle penetrates the wall of the vessel, the tip protector is extended past the tip of the needle to blunt the end of the needle. By protruding past the sharp tip of the needle, the tip protector protects the back wall of the vessel from accidental damage due to excessive advancement of the sharp tip of the needle following penetration.

DETAILED DESCRIPTION

A single-piece tool 10 is used to rapidly create an accurate, high-quality incision of a predefined length in a perfused or non-perfused vessel.

Figure 1:
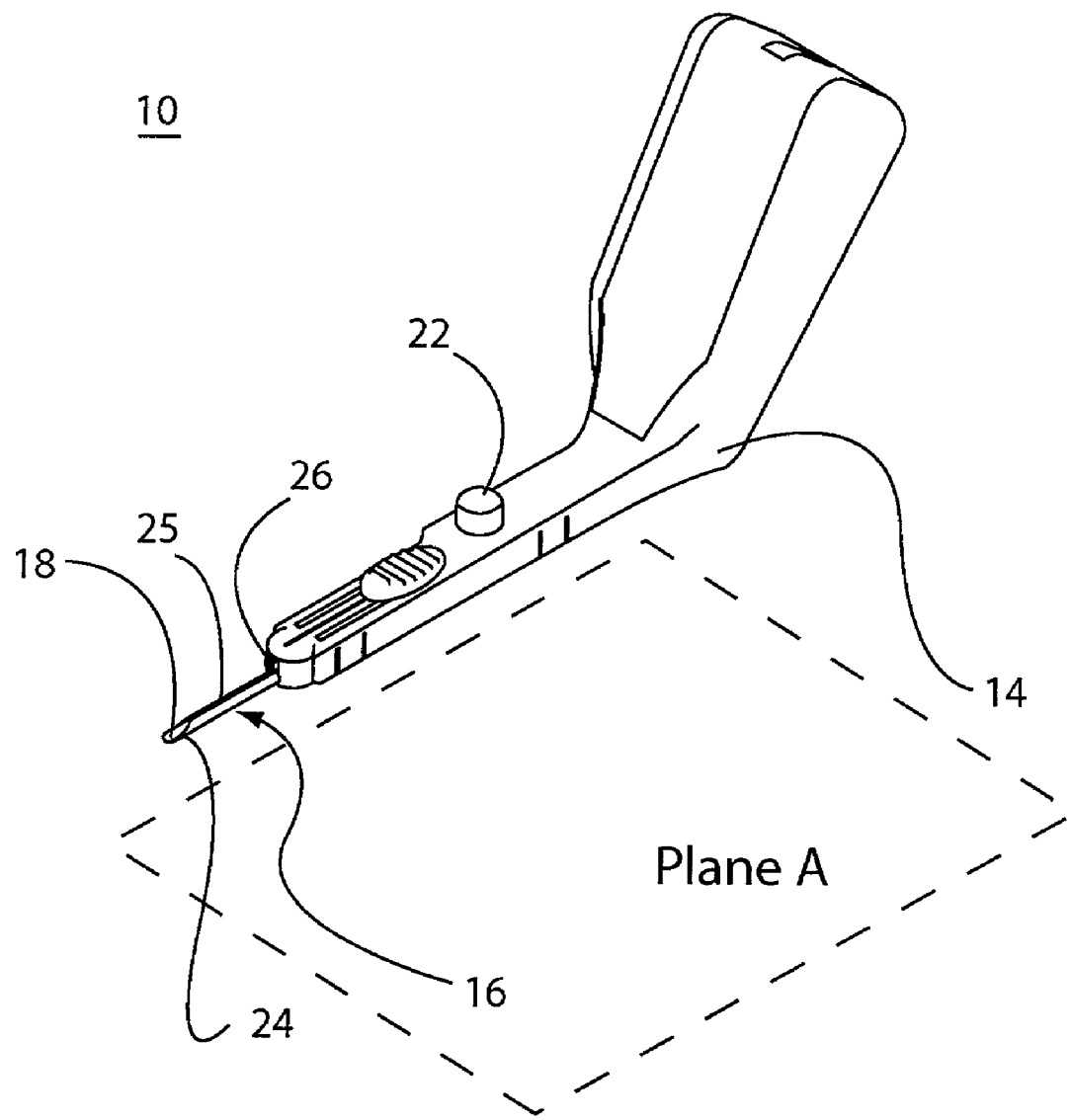
FIG. 1 is a perspective view of a tool for penetrating and creating an incision in a vessel in deployment position.

Referring to FIG. 1, a needle 16 is fixed to the distal end of a housing 14 of the tool 10. The needle 16 is a substantially cylindrical tube, but may have a different cross-section if desired. A single slot 25 along one side of the needle 16 extends from outside the needle into the lumen of the needle 16. The slot 25 extends substantially parallel to the axis of the needle 16. Alternatively, the slot 25 extends in a direction not substantially parallel to the axis of the needle 16 over at least a portion of its length. The tip 24 of the needle 16 is angled such that the slot 25 resides on the shortest side of the needle 16, with the longest side of the needle 16 being directly opposite the slot 25. Alternatively, the slot 25 has a different placement with regards to the orientation of the needle 16. Alternatively, there is more than one slot 25 through the needle 16. In addition, the tip 24 of the needle 16 may be shaped differently.

Figure 1A:
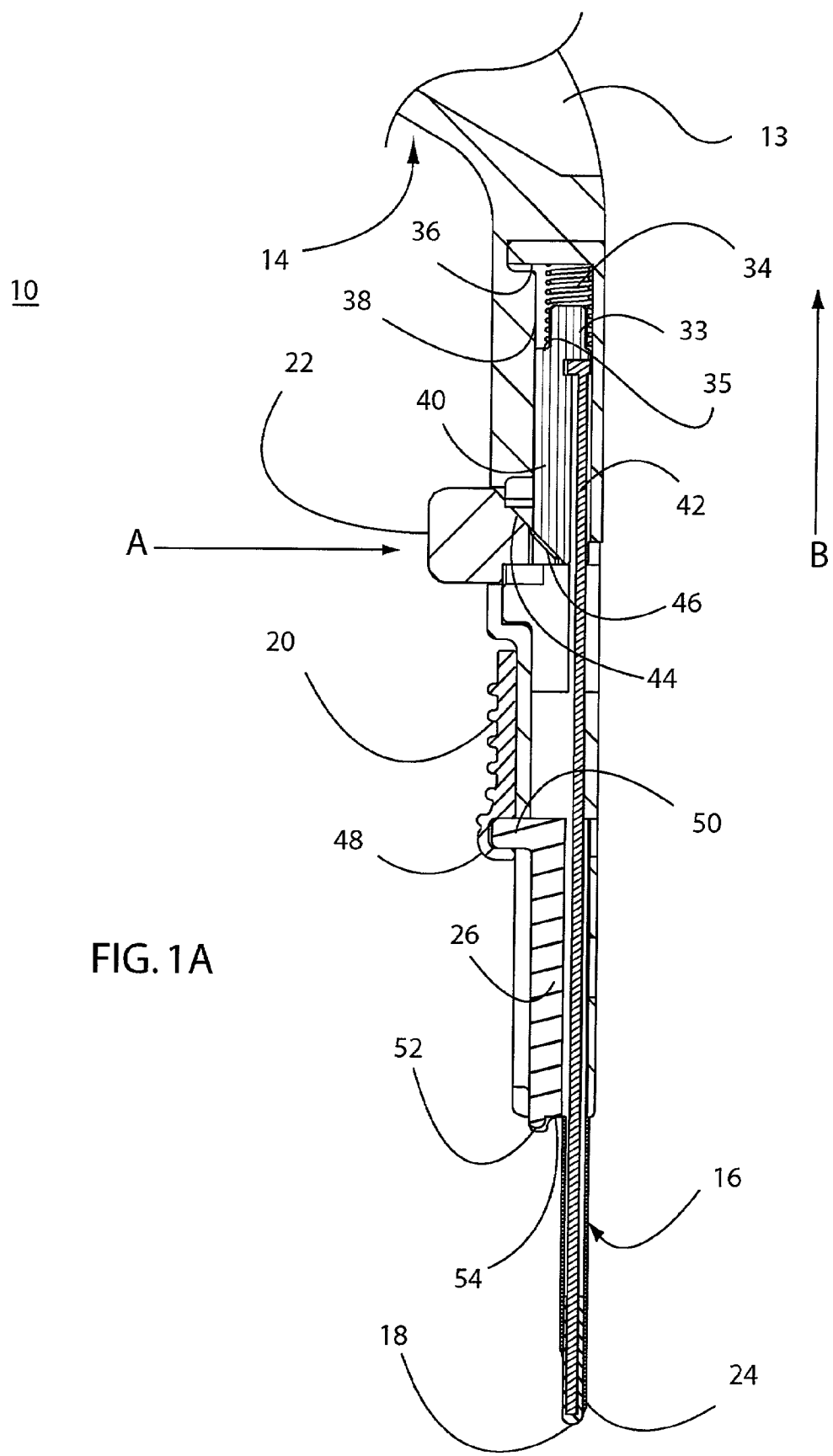
FIG. 1A is a side cross-sectional view of the tool.

Referring to FIG. 1A, the proximal end of the housing structure 14 terminates in a handle 13. The handle 13 is angled at approximately 120 degrees with respect to the remaining portion of the tool 10 to enable the user to easily reach the target vessel. The handle 13 may be angled or configured differently, or may be omitted altogether.

A first user input feature such as a button 22 controls the actuation of a tip protector 18. This is done via a cam 40. The cam 40 has a feature 33 at its proximal end that is slightly smaller in diameter than the inner diameter of a spring 34. One end of the spring 34 is connected to a surface 36 of a cavity 38 within the housing 14. The cam 40 itself is configured to translate within that cavity 38. The other end of the spring 34 holds the feature 33. The coils of the spring 34 act against a shoulder 35 of the cam 40. The spring 34 is a compression spring configured to bias the cam 40 toward the distal end of the housing 14.

Two flat, beveled surfaces 44 and 46 are substantially parallel to each other and roughly 45 degrees from the plane A as defined in FIG. 1. Plane A is arbitrarily defined as "horizontal" and the direction perpendicular to the plane A is arbitrarily defined as "vertical" in order to describe the structure and operation of the tool 10 clearly. These conventions are solely utilized to clarify this description, and do not limit the orientation of the tool 10 in use. The surfaces 44 and 46 instead may be oriented at a different angle from the one shown here. The first surface 44 is located on the underside of the button 22. The second surface 46 is located on the front portion of the cam 40. Prior to actuating the button 22, the two surfaces 44 and 46 may or may not be in contact with each other. As the button 22 is depressed, the surface 44 contacts and slides against the surface 46 on the distal portion of the cam 40. This sliding motion forces the cam 40 proximally, because the motion of the button 22 is substantially constrained to the vertical direction. When the button 22 is pushed by the user, the movement of the button 22 in the substantially vertical direction of arrow A causes the cam 40 to move in the substantially perpendicular horizontal direction indicated by arrow B. As the cam 42 translates proximally, it compresses the spring 34 that is attached to the surface 36 at the end of the cavity 38 within the tool housing 14. The two surfaces 44 and 46 continue to slide against each other until the button 22 is completely depressed and the overlapping areas of the two surfaces 44 and 46 are at a maximum.

The cam 40 holds one end of a wire 42. The other end of the wire 42 extends distal to the cam 40 and is attached to the tip protector 18. The wire 42 may alternately be any rigid structure that fits within the allotted space in the housing 14 and is moveable between a first position and a second position. Furthermore, the wire 42 can be made out of a variety of materials such as metal or plastic.

Figure 4:
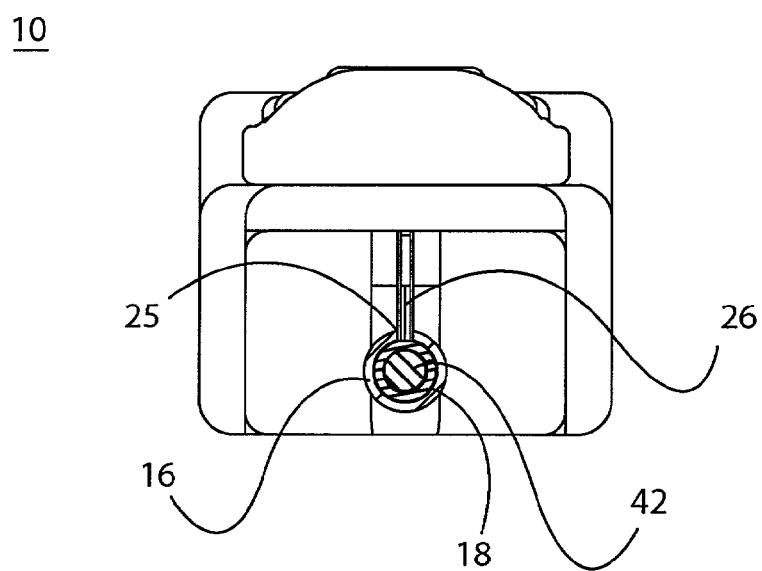
FIG. 4 is a front view of the tool.

Referring also to FIG. 4, the tip protector 18 is held by the lumen of the needle 16. The tip protector 18 is extendable beyond the tip 24 of the needle 16 to prevent the sharp tip 24 of the needle 16 from contacting the back wall of the vessel after initial penetration. The tip protector 18 is atraumatic to prevent injury to the back wall of the vessel. The back wall of the vessel is the wall of the vessel substantially opposite to the penetration made by the needle 16. The tip protector 18 has a circular cross-section with a substantially rounded end, but may have a different cross-sectional geometry if desired. A variety of different materials may be used to form the tip protector 18, including metal, plastic, ceramic, or rubber. Additionally, the tip protector 18 may be a coating created on the surface of the wire 42. Both the cam 40 and the wire 42 move together in a substantially linear motion to control the extension of the tip protector 18 from the tip 24 of the needle 16.

The tip protector 18 is located on the distal end of the wire 42 such that it extends past the tip 24 of the needle 16 when the spring 34 is in its relaxed state in a first position. When the button 22 is undepressed, the tip protector 18 is in the first position, at least partially outside but still coaxial with the lumen of the needle 16. When the button 22 is depressed, the tip protector 18 is moved to a second position substantially within the lumen of the needle 16.

Figure 2:
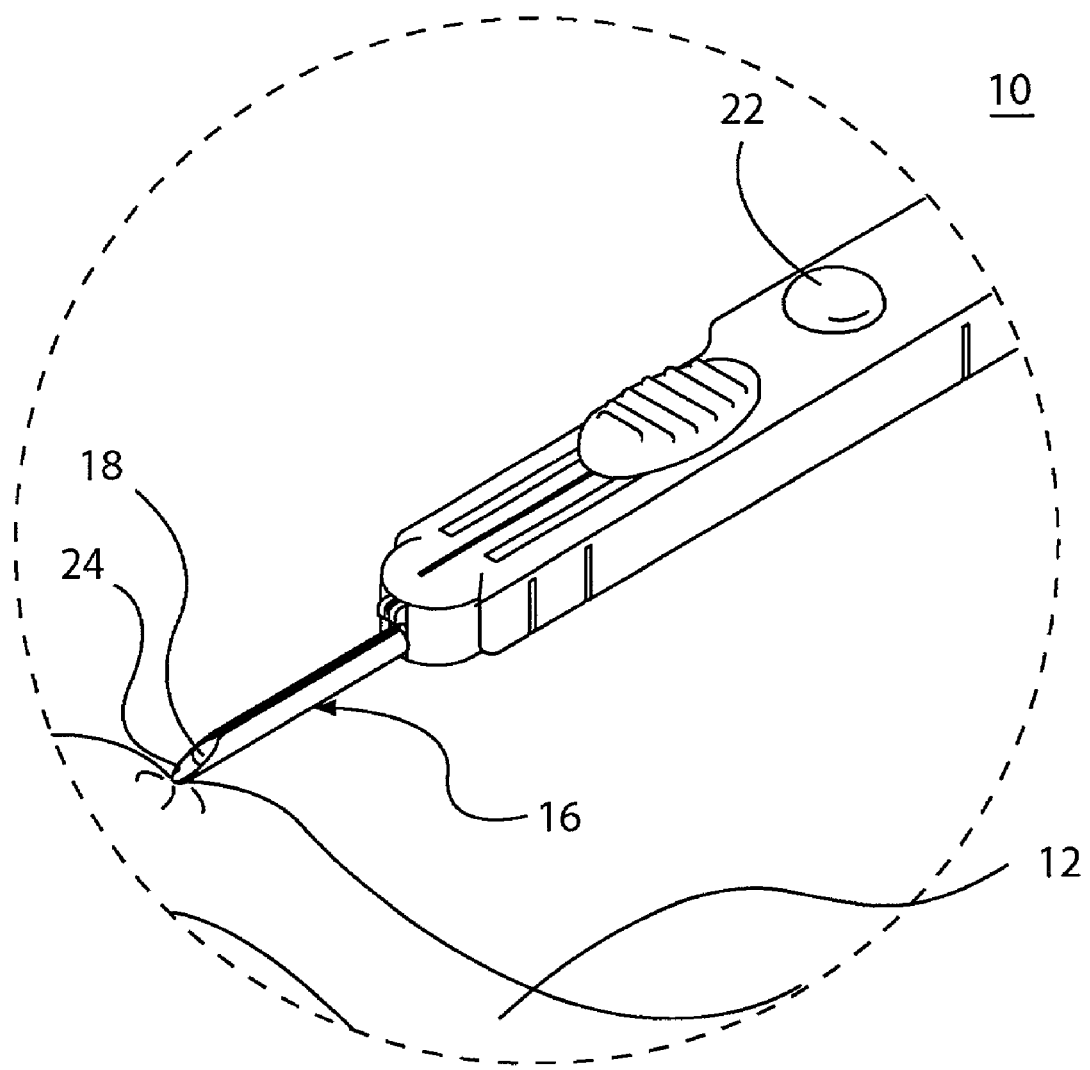
FIG. 2 is an enlarged perspective view of the distal portion of the tool with a tip protector retracted into a needle.
Figure 3:
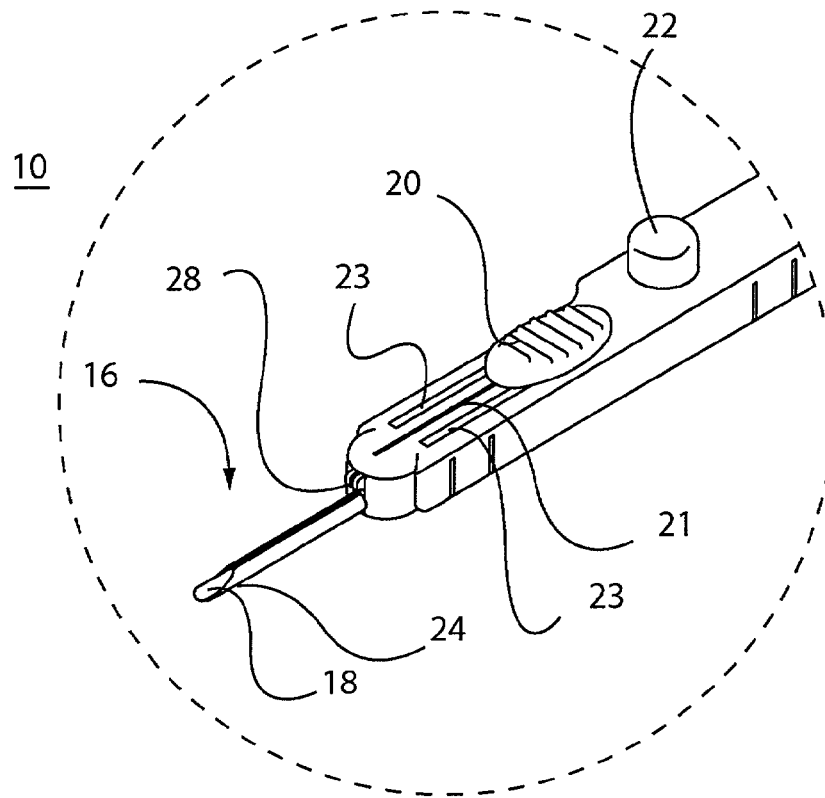
FIG. 3 is an enlarged perspective view of the distal portion of the tool with the tip protector extending past the tip of the needle.

Referring to FIG. 2, the tool 10 is positioned on the target vessel 12 immediately prior to penetration. Referring also to FIG. 1A, when the user pushes the button 22, the cam 40 moves proximally, thereby retracting the tip protector 18 into the needle 16 and exposing the sharp tip 24. The user then advances the entire tool 10 such that the sharp tip 24 penetrates the vessel wall 12. Vessel penetration may be confirmed visually by a small amount of blood or other fluids exiting the proximal end of the needle 16. Referring to FIG. 3, the button 22 is then released to allow the tip protector 18 to extend beyond the sharp tip 24 of the needle 16. This is desirable so as to prevent accidental penetration through the back wall of the vessel should the tool be advanced too far into the vessel. Referring back to the side cross-sectional view of FIG. 1A, the spring 34 returns to its normal, uncompressed state when the button 22 is released, thus causing the cam 40 and wire 42 to move distally and causing the tip protector 18 to extend past the tip 24 of the needle 16. Alternatively, the tip protector 18 may initially be retracted into the needle 16 and released or extended manually by the user following penetration into the vessel.

Referring to FIG. 4, the needle 16 is substantially coaxial with the wire 42 with a gap between them to accommodate the tip protector 18 attached to the wire 42. The outer diameter of the tip protector 18 may be substantially equal to the inner diameter of the needle 16, with adequate clearance between to allow the tip 18 to slide within the lumen of the needle 16. A cutting member 26 is held in and is moveable along the slot 25, the slot 25 serving to guide the cutting member 26 as it moves through the vessel and creates the incision. The slot 25 is substantially the same width as the cutting member 26 so as to maintain substantially linear movement of the cutting member 26 along the axis of the needle 16.

Figure 5:
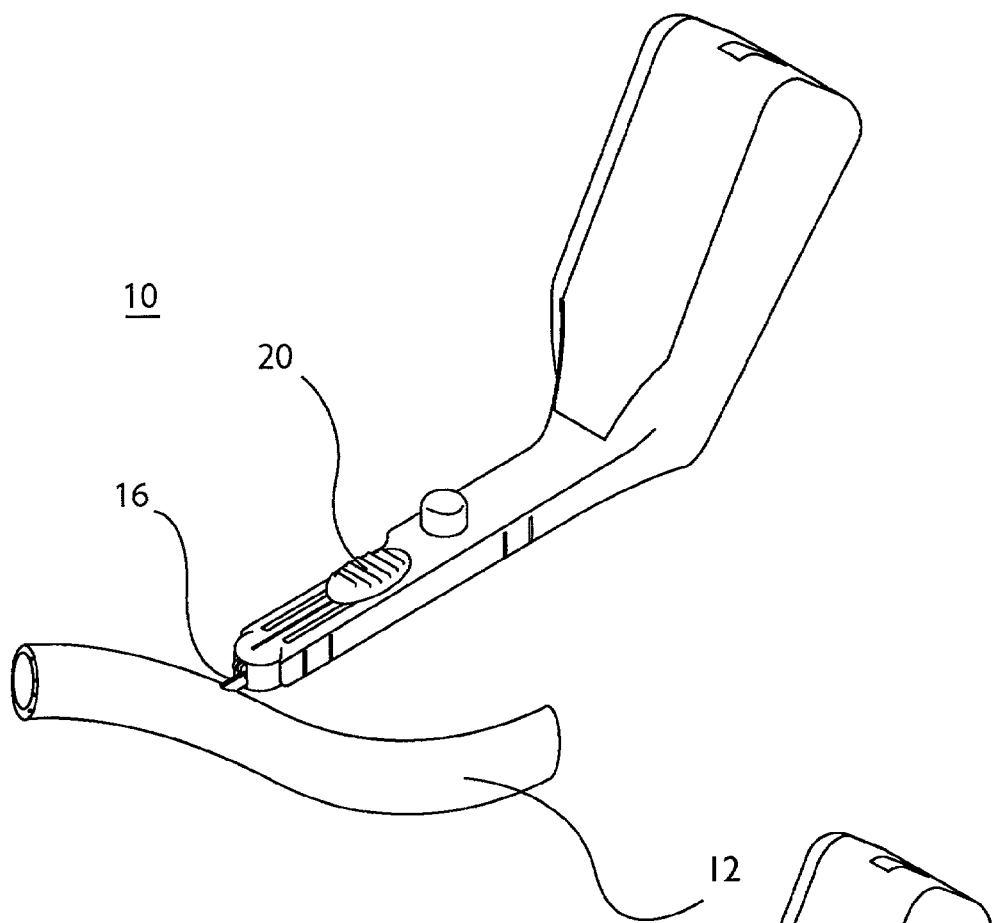
FIG. 5 is a perspective view of the tool with the needle fully inserted into the vessel.
Figure 6:
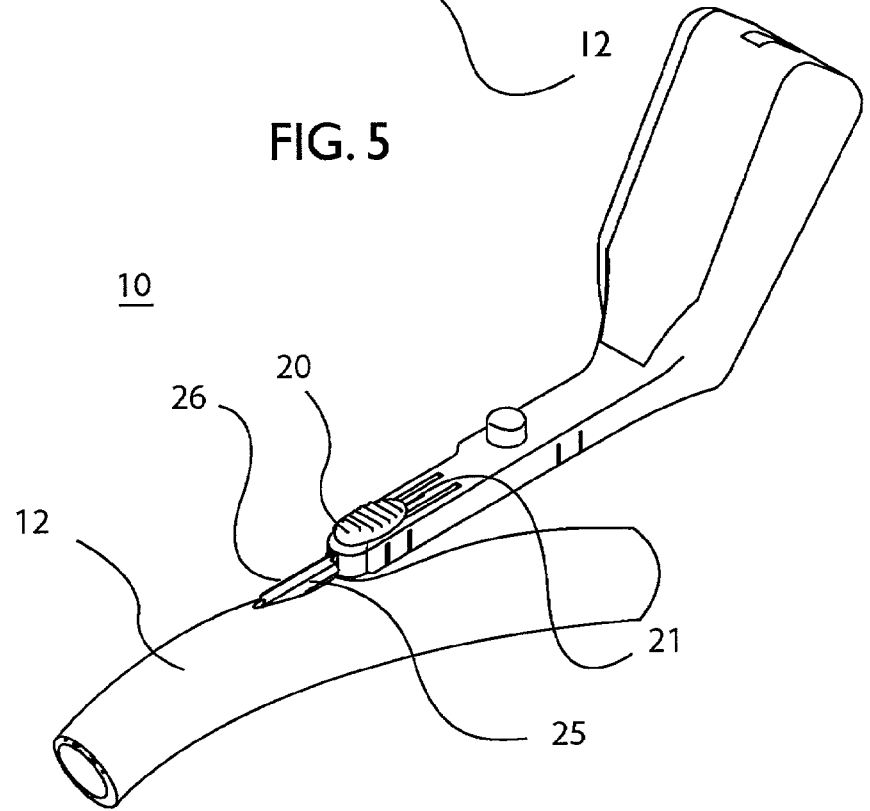
FIG. 6 is a perspective view of the tool with a cutting member moved forward to create the incision.

Referring to FIGS. 1A, 4, and 5, the needle 16 is inserted into the vessel 12. After the button 22 has been released to extend the tip protector 18, the surgeon actuates the cutting member 26 by using a second user input feature such as a slider 20 located at the distal end of the tool 10. The slider 20 is attached to the cutting member 26 such that moving the slider 20 translates the cutting member 26 along the slot 25 in the needle 16. Referring to FIG. 1A, an arched portion 48 on the slider 20 grips a tab 50 that is connected to the cutting member 26 such that linear movement of the slider 20 corresponds directly with linear movement of the cutting member 26 to create an incision in the vessel wall. Alternatively, the slider 20 may directly engage the cutting member 26 in a different way, or may indirectly engage the cutting member 26 such as by a linkage. The cutting member 26 has a nose 52 that engages the upper surface of the vessel while a sharpened edge 54 immediately beneath the nose 52 cuts through the vessel wall. The cutting member 26 may be made out of metal, ceramic, or other material whose edge can be made sharp. Referring also to FIG. 3, the tab 50 travels within a slot 21 in the tool housing 14 between an initial starting position and a final position. Additionally, there may be grooves 23 on either or both sides of the slot 23 to serve as tracks corresponding to features that may be present on the underside of the slider 20 to help guide the slider 20 as the surgeon creates the incision. the slider 20 is shown in the initial position. Referring to FIG. 6, the slider 20 is shown moved to the final position as the tool 10 is held within the vessel 12. Since the slot 21 is of a predefined length, the incision that is created by the cutting member 20 as the slider 20 is moved from the initial position to the final position will be of a known length and no measurements are needed on the part of the surgeon prior to or during the procedure.

Figure 7:
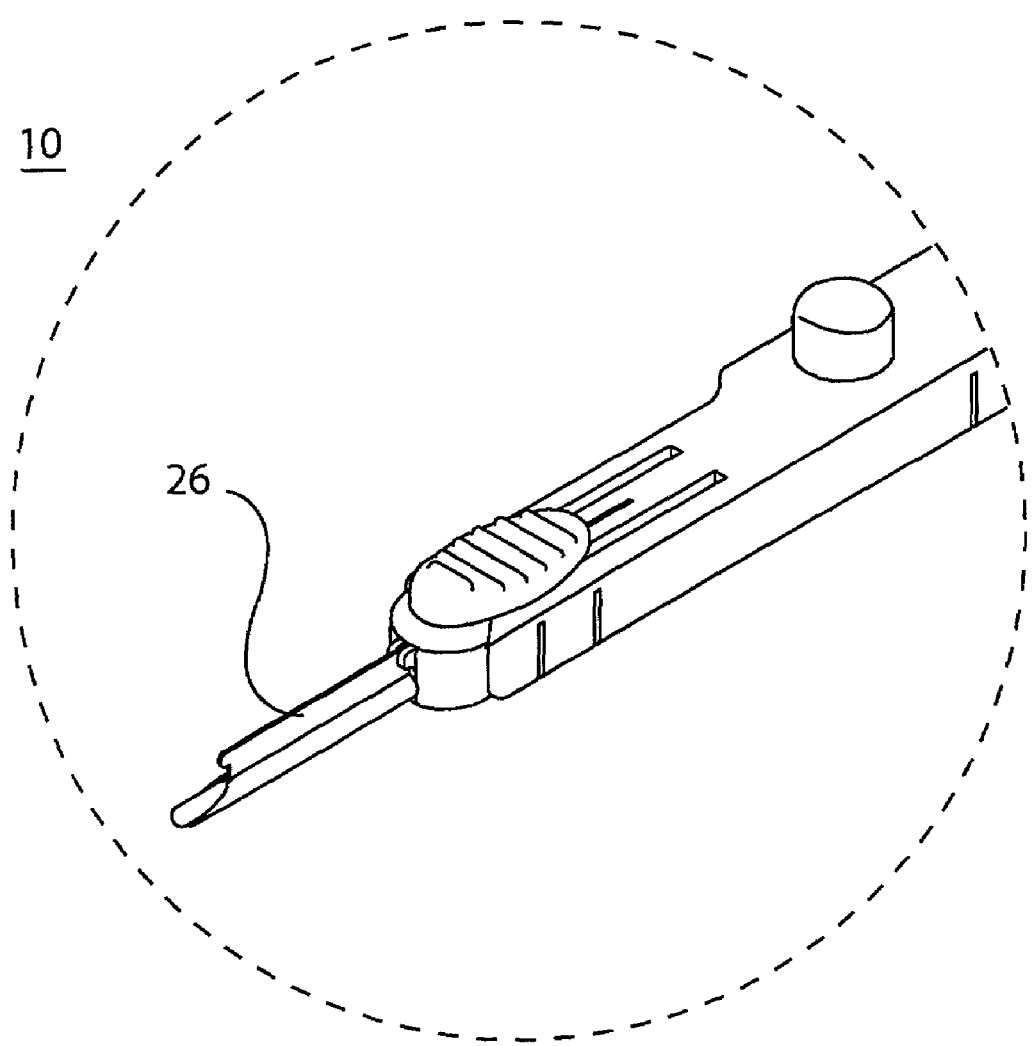
FIG. 7 is a perspective view of the tool after the cutting member has been deployed.

Referring to FIG. 7, the cutting member 26 is shown fully deployed. The tool 10 is then removed from the newly created incision. Where the incision is an arteriotomy performed before anastomosis, a graft vessel is attached to complete the anastomosis.

While the invention has been described in detail, it will be apparent to one skilled in the art that various changes and modifications can be made and equivalents employed, without departing from the present invention. For example, while the tool has been described in terms of cutting a blood vessel, other tissue could be cut with it as well. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A surgical tool for creating an arteriotomy, comprising:
   a tubular needle including a tube wall and a lumen defined therein, wherein a slot extends through said tube wall;
   a tip protector moveable with respect to said needle;

a cutting member moveable with respect to said needle, wherein said cutting member includes a sharpened edge movable through said slot and a nose; and a housing holding said needle and said cutting member.

2. The surgical tool of claim 1, wherein said needle is fixed to one end of said housing.

3. The surgical tool of claim 1, wherein said needle and said tip protector are substantially coaxial.

4. The surgical tool of claim 1, further comprising a first user input feature connected to said housing and configured to actuate said tip protector.

5. The surgical tool of claim 4 further comprising a second user input feature connected to said cutting member and slideable relative to said housing.

6. The surgical tool of claim 1, wherein an end of said needle is beveled.

7. A method for making an incision in a tubular vessel, comprising:

penetrating a target vessel with a tubular needle having a tube wall and a lumen defined therein, wherein a slot extends through said tube wall;

moving a tip protector relative to said needle before said penetrating; and actuating a cutting member movable along said slot.

8. The method of claim 7, wherein said actuating comprises translating said cutting member along said slot.

9. The method of claim 7, further comprising moving said tip protector relative to said needle after said penetrating.

* * * * *